US009763603B2

(12) United States Patent
Rosenblood

(10) Patent No.: US 9,763,603 B2
(45) Date of Patent: Sep. 19, 2017

(54) POSTURE IMPROVEMENT DEVICE, SYSTEM, AND METHOD

(71) Applicant: Kenneth Lawrence Rosenblood, Los Angeles, CA (US)

(72) Inventor: Kenneth Lawrence Rosenblood, Los Angeles, CA (US)

( * ) Notice: Subject to any disclaimer, the term of this patent is extended or adjusted under 35 U.S.C. 154(b) by 0 days.

(21) Appl. No.: 14/918,334

(22) Filed: Oct. 20, 2015

(65) Prior Publication Data

US 2016/0110986 A1   Apr. 21, 2016

Related U.S. Application Data

(60) Provisional application No. 62/066,800, filed on Oct. 21, 2014.

(51) Int. Cl.
*G08B 23/00* (2006.01)
*A61B 5/11* (2006.01)
*A61B 5/103* (2006.01)
*A61B 5/00* (2006.01)

(52) U.S. Cl.
CPC ............ *A61B 5/1116* (2013.01); *A61B 5/103* (2013.01); *A61B 5/486* (2013.01); *A61B 5/74* (2013.01)

(58) Field of Classification Search
CPC ....... A61B 5/103; A61B 5/1116; A61B 5/486; A61B 5/74
USPC ....................................................... 340/573.7
See application file for complete search history.

(56) References Cited

U.S. PATENT DOCUMENTS

| 4,750,480 A | 6/1988 | Jenness |
| 5,402,107 A | 3/1995 | Rencavage |
| 5,425,378 A | 6/1995 | Swezey |
| 5,459,676 A | 10/1995 | Livingston |

(Continued)

FOREIGN PATENT DOCUMENTS

| EP | 2706325 | 3/2014 |
| JP | 2014075964 | 4/2014 |

(Continued)

OTHER PUBLICATIONS

PCT International Search Report, Jan. 26, 2016.
(Continued)

*Primary Examiner* — Ojiako Nwugo
(74) *Attorney, Agent, or Firm* — Hankin Patent Law APC; Kevin Schraven; Anooj Patel

(57) ABSTRACT

A posture improvement device, system, and method. The system for improving posture may comprise: a sensor device; posture improvement software program, comprising a posture improvement system interface; and one or more user devices. The sensor device may be physically associated with a user and may communicate with the posture improvement software program. The sensor device may comprise: one or more sensors for monitoring positions and movements of the user. The system may calculate one or more optimum postural positions for the user, based on data communicated by the sensor device and collected information about the user. The system may monitor a conformance of the user with the optimum postural positions and may display the conformance on the posture improvement system interface. The system may detect and notify the user of one or more non-conformances, such that a user is reminded to maintain at least one optimum postural position.

8 Claims, 12 Drawing Sheets

(56) References Cited

U.S. PATENT DOCUMENTS

| | | |
|---|---|---|
| 5,749,838 A | 5/1998 | Kline |
| 5,930,741 A | 7/1999 | Kramer |
| 5,941,836 A | 8/1999 | Friedman |
| 6,059,576 A | 5/2000 | Brann |
| 6,426,719 B1 | 7/2002 | Nagareda |
| 6,554,781 B1 | 4/2003 | Carter |
| 6,682,351 B1 | 1/2004 | Abraham-Fuchs |
| 6,703,939 B2 | 3/2004 | Lehrman et al. |
| 6,834,436 B2 | 12/2004 | Townsend |
| 6,864,796 B2 | 3/2005 | Lehrman et al. |
| 7,095,331 B2 | 8/2006 | Lehrman et al. |
| 7,145,461 B2 | 12/2006 | Lehrman |
| 7,210,240 B2 | 5/2007 | Townsend |
| 7,292,151 B2 | 11/2007 | Ferguson |
| 7,400,259 B2 | 7/2008 | O'Connor |
| 7,471,290 B2 | 12/2008 | Wang |
| 7,479,890 B2 | 1/2009 | Lehrman et al. |
| 7,503,878 B1 | 3/2009 | Amsbury |
| 7,602,301 B1 | 10/2009 | Stirling et al. |
| 7,625,316 B1 | 12/2009 | Amsbury |
| 7,658,695 B1 | 2/2010 | Amsbury |
| 7,698,830 B2 | 4/2010 | Townsend |
| 7,771,318 B2 | 8/2010 | Narayanaswami |
| 7,843,351 B2 | 11/2010 | Bourne |
| 7,850,574 B2 | 12/2010 | Narayanaswami |
| 8,036,826 B2 | 10/2011 | MacIntosh |
| 8,043,173 B2 | 10/2011 | Menalagha |
| 8,083,693 B1 | 12/2011 | Mckeon |
| 8,085,153 B2 | 12/2011 | O'Connor |
| 8,165,840 B2 | 4/2012 | Hatlestad |
| 8,217,797 B2 | 7/2012 | Ikoyan |
| 8,284,070 B2 | 10/2012 | Chaudhari |
| 8,366,641 B2 | 2/2013 | Wang |
| 8,436,737 B1 | 5/2013 | Trout |
| 8,441,343 B1 | 5/2013 | Fishman |
| 8,579,834 B2 | 11/2013 | Davis |
| 8,643,494 B1 | 2/2014 | Trout |
| 8,684,922 B2 | 4/2014 | Tran |
| 8,688,225 B2 | 4/2014 | Panken |
| 8,747,336 B2 | 6/2014 | Tran |
| 8,818,748 B2 | 8/2014 | Hatlestad |
| 8,932,236 B1 | 1/2015 | Mckeon |
| 9,028,407 B1 | 5/2015 | Bennett-Guerrero |
| 9,035,794 B2 | 5/2015 | Narasimhan et al. |
| 9,128,521 B2 | 9/2015 | Chang et al. |
| 9,149,211 B2 | 10/2015 | Mravyan |
| 9,174,055 B2 | 11/2015 | Davis |
| 9,207,268 B2 | 12/2015 | Fujiwara |
| 2006/0129059 A1 | 6/2006 | Kim et al. |
| 2006/0195051 A1 | 8/2006 | Schnapp |
| 2007/0013651 A1 | 1/2007 | Depue |
| 2007/0032748 A1 | 2/2007 | McNeil |
| 2007/0149360 A1* | 6/2007 | Narayanaswami .... A63B 24/00 482/8 |
| 2009/0054814 A1 | 2/2009 | Schnapp |
| 2009/0324024 A1* | 12/2009 | Worthington .......... A61B 5/103 382/118 |
| 2011/0275939 A1* | 11/2011 | Walsh ................. A61B 5/4561 600/473 |
| 2013/0201021 A1 | 8/2013 | Limonadi |
| 2013/0207889 A1* | 8/2013 | Chang ................. A61B 5/0002 345/156 |
| 2014/0015687 A1 | 1/2014 | Narasimhan et al. |
| 2014/0019080 A1 | 1/2014 | Chan et al. |
| 2014/0070790 A1 | 3/2014 | Fujiwara et al. |
| 2014/0119080 A1* | 5/2014 | Sakamoto ............. H02M 7/493 363/95 |
| 2014/0129178 A1* | 5/2014 | Meduna ................. G06F 17/00 702/189 |
| 2014/0141881 A1 | 5/2014 | Brick |
| 2014/0152443 A1 | 6/2014 | Cammans |
| 2014/0326084 A1 | 11/2014 | Bhushan |
| 2015/0065919 A1* | 3/2015 | Cuevas ................. A61B 5/1116 600/587 |
| 2015/0272481 A1 | 10/2015 | Glaser |

FOREIGN PATENT DOCUMENTS

| | | |
|---|---|---|
| KR | 20-0207264 | 12/2000 |
| KR | 200207264 | 12/2000 |
| KR | 10-0657917 | 12/2006 |
| KR | 100657917 | 12/2006 |
| WO | WO 0137730 | 5/2001 |
| WO | 2014011343 | 1/2014 |
| WO | WO 2014125448 | 8/2014 |
| WO | WO 2014193824 | 12/2014 |
| WO | WO 2014035922 | 6/2015 |
| WO | WO 2015079436 | 6/2015 |
| WO | WO 2015097689 | 7/2015 |

OTHER PUBLICATIONS

Lumo, Lumo Bodytech—Makers of the Lumo Lift Posture Coach, 2015, Lumo Bodytech Inc. brochure http://www.lumobodytech.com/?gclid=CjwKEAjwkK6wBRCcoK_tiOT-zFASJAC7RAriz3wcNtVdUpdyvOPSqjZCHV7Jg8pvVZd7YeTC8p0cBoCn-7Dw_wcB.

Lumo, Lumo Lift, Oct. 1, 2014, Lumo Bodytech Inc. brochure. http://www.lumobodytech.com/.

Lee, Lee, Choi & Shim—Smart Pose: Mobile Posture-aware System for Lowering Physical Health Risk of Smartphone Users http://altchi.org/2013/submissions/submission_lhs2008_0.pdf.

Patent Cooperation Treaty, International Preliminary Report on Patentability, Apr. 25, 2017, Korean Intellectual Property Office.

* cited by examiner

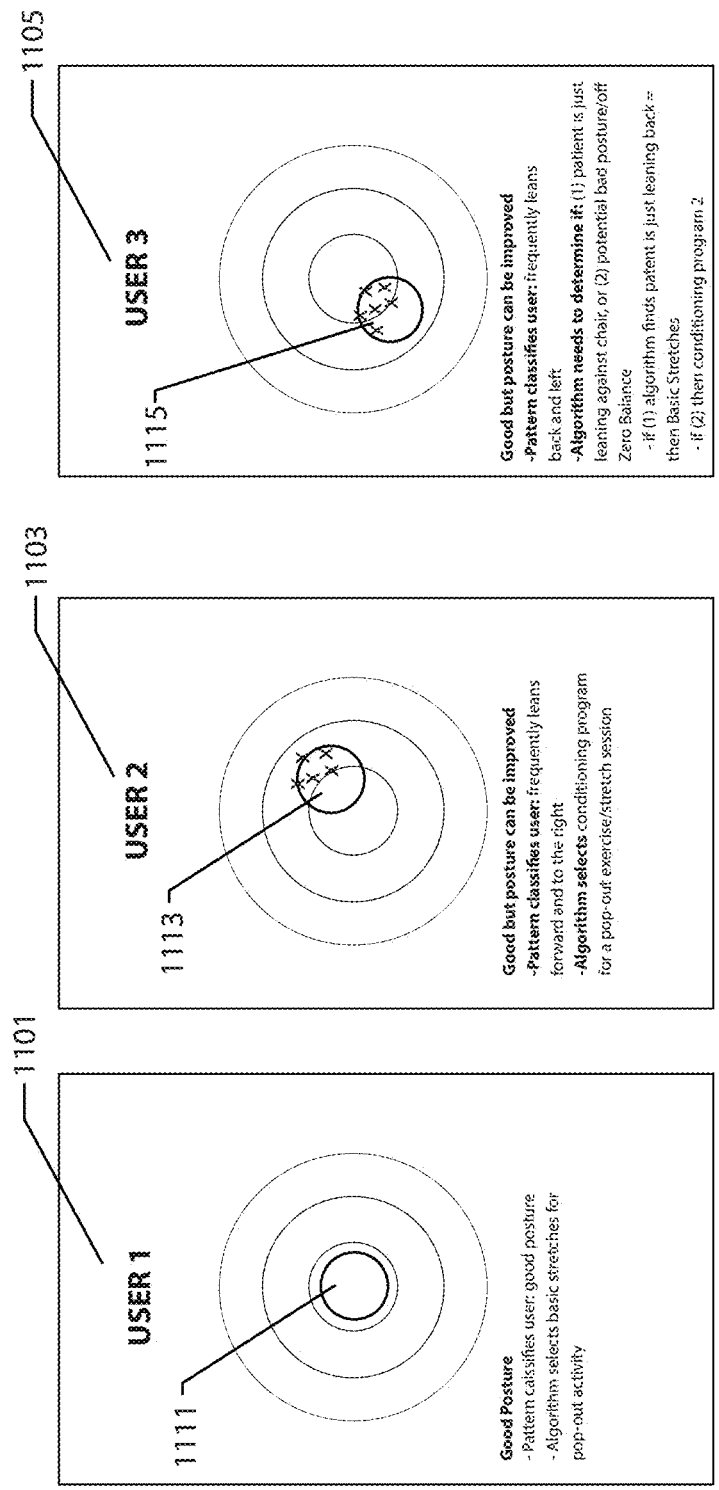

POSTURE IMPROVEMENT DEVICE, SYSTEM, AND METHOD

CROSS REFERENCE TO RELATED APPLICATIONS

This application claims the benefit of U.S. Provisional Patent Application No. 62/066,800, filed on Oct. 21, 2014, by inventor Kenneth Rosenblood, entitled POSTURE IMPROVEMENT SYSTEM, the entire contents and substance of which are hereby incorporated in total by reference, and to which priority is claimed.

FIELD OF USE

The present disclosure relates generally to systems for improving posture, and more particularly, to systems that conditions a user to practice improved posture through real-time viewing monitoring of their own posture, warnings, reminders to exercise and stretch programs, and behavioral modification.

BACKGROUND

There is a strong correlation between good posture and good health. Many productive hours are lost each year due to pain and sickness associated with posture-induced health issues. Improved posture has been shown to increase levels of dopamine and testosterone produced by the brain, and research has indicated that correction of postural kyphosis in patients with ADHD may lead to a significant reduction of ADHD symptoms. When people operate with good posture, research indicates that performance regarding mental acuity, self-esteem, and physiological efficiency is improved. Thus, providing insight and a mechanism for improving posture has been a desirable goal for many people as it improves mental performance and overall health.

Unfortunately, the demands of the modern work environment have resulted in poor posture for many individuals. Whether caused by a chronically incorrect static body position at a workstation, limited motion while at the workstation, or a repetitive motion induced by an occupational requirement, the modern work environment has contributed to improper posture for millions of people, which has negatively impacted the health of those millions of people. This poor posture is increasing and being further exacerbated by the increased use of devices such as smart devices, both in all facets of our lives. Despite the wide range of information provided by these electronic devices, they have yet to provide corrective insight towards improving the health of the user by an effective posture conditioning program, such as teaching the user new things about themselves and new habits.

Every person has four to eight positions in which they spend a predominant majority of their waking time. Each represents an opportunity to establish the most optimum position for physical and mental function. They are distinct Optimum Postural Positions (OPP) that are determined by that person's individual anatomy and the specific task performed by that person (whether occupational or leisure). Most people have a minimum of five physical positions where they spend 80% of their time—i.e. computer data input, driving, walking. As a result, these positions, if held incorrectly, may negatively impact overall health and mental performance of the person. Unfortunately, even once a person is aware of his or her OPP, it is difficult for that person to change his/her postural behavior due to a lack of insight, understanding, and neuromuscular sensation of what good posture is. Thus, there is a need to teach, condition, and train an individual to overcome poor habits in order to maintain his or her various OPP through a gradual exercise, movement and strength training program, resulting in insight by the user into their own neuromuscular system and good habits.

Currently, many individuals are aware of their bad posture as a manifestation of the pain or discomfort they suffer. These individuals, however, lack the insight of how to correct their posture because they do not know their OPP, how to maintain their OPP, and/or are not even aware when they are not in their OPP.

Therefore, there is a need for a device, system, and method that can identify an individual's OPP, teach an individual to maintain their OPP, and monitor an individual's posture in order to expose them to proper posture in real time and alert them when they are not properly practicing their OPP. Preferably, the new device, system, and method will: (1) identify the OPP of an individual; (2) insight and neuromuscular sensation of being in OPP and falling out of OPP; (3) encourage an individual to practice their OPP; (4) monitor the postural behavior of an individual; and (5) provide movement, stretching, and strength conditioning programs based on recorded posture behaviors of the individual.

SUMMARY OF EMBODIMENTS

To minimize the limitations in the prior art, and to minimize other limitations that will become apparent upon reading and understanding the present disclosure, the present specification discloses a new and improved device, system, and method for improving posture.

The posture improvement system may comprise a sensor device, a user device and software that calculate optimal postural positions and allow a user to maintain the different optimal postural positions (OPP) they frequent most, through real time feedback, warnings, and reminders.

It is an object to provide a device, system, and method for improving the posture of a user.

It is an object to provide a device, system, and method configured to: (1) identify the OPP of an individual; (2) teach by providing insight to the user to practice their OPP; (3) monitor the postural behavior of an individual in real-time; and (4) record postural patterns over time to develop improved posture conditioning programs for the user.

It is an object to provide a device, system, and method configured to correct the posture of a user through behavioral modification.

It is an object to provide a device, system, and method configured to correct the posture of a user through the use of negative feedback, positive feedback, and neuromuscular conditioning.

It is an object to provide one or more sensors configured to measure the weight, pressure, the orientation, steps, the heart rate, the blood pressure, the gyroscopic orientation, and the respiration of a user.

It is an object to provide a new and improved device, system, and method that facilitates a user to correct his or her posture.

It is an object to overcome the deficiencies of the prior art.

One embodiment of the system for improving posture may comprise: a sensor device; a posture improvement software program, which comprises a posture improvement system interface; and one or more user smart devices. The sensor device may be configured to be physically associated with a user. The sensor device communicates with the posture improvement software program. The sensor device comprises: one or more sensors, which when physically associated with the user, monitor a physical position of the user and one or more movements of the user. The posture improvement software program may be configured to operate on the one or more user smart devices. The posture improvement system interface may be displayed to the user on the one or more user smart devices. The software program may be configured to collect information about the user. The system for improving posture calculates one or more optimum postural positions for the user, based on data communicated by the sensor device and the collected information about the user. The system for improving posture monitors a conformance of the user with at least one of the one or more optimum postural positions. The system for improving posture displays the users conformance on the posture improvement system interface. The posture improvement system detects and notifies the user of one or more non-conformances, such that a user may be reminded to maintain the at least one of the one or more optimum postural positions. The displaying of the conformance of the user with at least one of the one or more optimum postural positions is via a target and a posture target ball. The posture target ball may be substantially within a center of the target when the user may be in the conformance with the at least one of the one or more optimum postural positions. When the user fails to maintain the at least one of the one or more optimum postural positions, the posture target ball is not substantially within the center of the target and posture improvement system interface notifies the user of the one or more non-conformances. When the user fails to maintain the at least one of the one or more optimum postural positions, the user device may be substantially disabled until the user corrects the non-conformance. The notifying of the user of the one or more non-conformances may be selected from the group of notifications consisting of: a sound; a flash of light; a vibration; and a color change of the posture improvement system interface. The posture improvement system interface comprises: a target; a target posture ball; an instructions screen; a warning settings screen; a devices screen; and an optimum postural position settings (which may be named by the user by activity) screen. The one or more optimum postural positions may be selected by the user and by position associated with any activity, from the positions consisting of: a seated position; a reading position; a working position; a seated typing position; a phone use position; a standing position; a walking position; and a relaxing position. The one or more user devices may be selected from the group of devices consisting of: a smart phone; a laptop computer; a smart television; a mouse; a monitor; a chair; a tablet; a smart watch; a keyboard; eyewear, and a computer. A sensitivity of the notifying of the one or more non-conformances may be adjustable. The posture improvement software program further comprises an activity notification. The activity notification requires the user to perform a movement of the user's body such that the target posture ball moves along a suggested path on the target.

Another embodiment may be a sensor device for improving posture, comprising: one or more sensors; a communication device; and a harness. The harness may be configured to allow the sensor device to be worn by a user. The communication device may be configured to communicate with one or more user devices. The one or more sensors detect a physical position of the user and one or more movements by the user, such that a plurality of sensor data may be created. The communication device transmits the plurality of sensor data to the one or more user devices. The detection and transmission of the plurality of sensor data may be configured to allow the user to maintain one or more optimum postural positions. The sensor device may further comprise a memory unit; wherein the memory unit stores the plurality of sensor data. The one or more sensors comprise: a plurality of accelerometers and a plurality of gyroscopes. The plurality of accelerometers comprise three tri-axial accelerometers and the plurality of gyroscopes comprise three tri-axial rate gyroscopes. The harness may be poseable, conforms to the user, and hooks over both shoulders of the user. The harness may be configured to securely hold the one or more sensors between the first and the tenth thoracic vertebrae of the user. The harness may be an article of clothing. The posture improvement software system may comprise a conditioning program. The conditioning program may recommend an interval program based on a postural behavior of the user; and the conditioning program provides insight to the user regarding the postural behavior of the user.

Another embodiment of the system for improving posture may comprise: a smart phone; and a posture improvement software program operating on the smart phone. The smart phone comprises at least one accelerometer and at least one gyroscope. The posture improvement software program uses the at least one accelerometer and the at least one gyroscope to determine an optimum phone position when the phone is being used by a user. The posture improvement software program requires the user to maintain the optimum phone position, such that when the optimum phone position is not maintained, the posture improvement software program temporarily disables the smart phone at least until the smart phone is returned to the optimum phone position In other embodiments the phone may not be disabled but other notifying events may be set by user.

Another embodiment of the system for gradually improving posture may comprise: a smart phone or other user device; a posture improvement software program operating on the smartphone or other user device; and information gathered by the user regarding physical body type and size, physical capabilities, and goals of the user. The information gathered from the user is utilized by the posture improvement software program to form a gradual exercise, stretch, and conditioning program such that proper posture achieved in a safe manner. The gradual conditioning program is separated into three consecutive phases: stretch and activity phase, time spent in perfect posture phase, and a phase of good, but chair supported posture. The gradual conditioning program will determine through algorithm the ratio of time spent in each phase such that the user can gradually build muscle capacity to perform perfect posture for longer periods of time. Example 1: if the user is really strong then the program may comprise a 5 minute stretch, 30 minutes perfect posture, and 25 minutes relaxed posture (cycle time 1 hour). Over time, the program may change to a 5 minute stretch, 50 minutes perfect posture, and a 5 minute relaxed posture, and so on. Example 2: if the beginning user is relatively weak with limited mobility, the program may start with a 10 minute stretch, 10 minutes of perfect posture, and 40 minutes of relaxed posture. Over time, the program may increase difficulty to 10 minutes of stretch, 20 minutes of perfect posture, and 30 minutes relaxed posture, and so on. This embodiment may also include an intensive conditioning program at the initiation of an OPP setting—i.e. at a work station. This feature may require a higher ratio of perfect posture time phase, and less time spent in stretch and relaxed posture. Subsequently, the gradual conditioning program will be resumed for the remainder of time spent at the workstation.

Another embodiment of this system comprises: a smart phone or other user device; a target and target ball displayed on a smartphone or other user device; tracking of the target ball on the display temporally to relay posture behavioral patterns; and a posture software conditioning program. The temporal tracking of the target ball will allow the user to recognize their own postural behavior patterns. In addition, temporal tracking of the target ball will allow the posture software conditioning program to select a specific conditioning activity to correct improper posture.

Another embodiment may be a device, system, and/or method for improving posture, comprising: one or more sensor; a software program, a computer, and an indicator; wherein the one or more sensor may be configured to monitor posture of a user; wherein the software program may be configured to run on the computer; wherein the software program may be configured to accept information about the user; wherein the software program may be configured to calculate an optimum postural position based on measurements collected by the one or more sensor and the information about the user; wherein the one or more sensor may be configured to monitor conformance of the user with the calculated optimum postural position and may send information on conformance of the user with the calculated optimum postural position to the software program; wherein the software program may be configured to prompt the indicator to provide a signal to the user. The one or more sensor may be configured to determine a weight, a pressure, an orientation, a heart rate, a blood pressure, a gyroscopic orientation, and a respiration of the user. The system may further comprise a camera; wherein the software program may be configured to accept data from the camera; wherein the software program may be configured to calculate the optimum postural position based on measurements collected by the one or more sensor, data from the camera, and the information about the user; wherein the camera may be configured to monitor conformance of the user with the calculated optimum postural position. The indicator may comprise: a screen, a speaker, and a sensor; wherein the screen may display a visual signal in response to the one or more sensor detecting that the user is not in the calculated optimum postural position; wherein the speaker may provide an auditory signal in response to the one or more sensor detecting that the user is not in the calculated optimum postural position; and wherein the one or more sensor may provide a tactile signal in response to the sensor detecting that the user is not in the calculated optimum postural position. The indicator may also comprise one or more computer accessory; wherein the one or more computer accessory may cease to function in response to the one or more sensor detecting the user is not in the calculated optimum postural position; wherein the one or more computer accessory may function in response to the one or more sensor detecting the user has returned to the calculated optimum postural position. The one or more sensor may comprise a means of affixing; wherein the means of affixing may comprise an adhesive, a hook and loop, a button, and a snap. The system for improving posture may comprise six sensors, wherein the six sensors may comprise: a first sensor, a second sensor, a third sensor, a fourth sensor, a fifth sensor, and a sixth sensor; wherein the first sensor may be configured to be located under a right sits bone of the user; wherein the second sensor may be configured to be located under a left sits bone of the user; wherein the third sensor may be configured to be located under a right foot of the user; wherein the fourth sensor may be configured to be located under a left foot of the user; wherein the fifth sensor may be configured to be located on a right shoulder of the user; and wherein the sixth sensor may be configured to be located on a left shoulder of the user. The software program may be configured to store data from the one or more sensor; wherein the software program may be configured to provide real-time feedback on posture of the user. The software program may be configured to analyze the information from the one or more sensor and provide a suggestion of an appropriate stretch and an appropriate exercise required for the user to improve conformance with the calculated optimum postural position.

Another embodiment of the device, system, and/or method for improving posture, may comprise: one or more initial sensor, one or more aligning sensor, a software program, a computer, and an indicator; wherein the one or more initial sensor may be configured to monitor an initial posture of a user; wherein the software program may be configured to run on the computer; wherein the software program may be configured to accept information about the user; wherein the software program may be configured to calculate an optimum postural position based on measurements collected by the one or more initial sensor and the information about the user; wherein the one or more aligning sensor may be configured to monitor conformance of the user with the calculated optimum postural position and send information on conformance of the user with the calculated optimum postural position to the software program; wherein the software program may be configured to prompt the indicator to provide a signal to the user. The one or more initial sensor may be configured to determine a weight, a pressure, an orientation, a heart rate, a blood pressure, a gyroscopic orientation, and a respiration of the user. The system may further comprise a camera; wherein the software program may be configured to accept data from the camera; wherein the software program may be configured to calculate the optimum postural position based on measurements collected by the one or more initial sensor, data from the camera, and the information about the user; wherein the camera may be configured to monitor conformance of the user with the calculated optimum postural position. The indicator may comprise: a screen, a speaker, and one or more aligning sensor; wherein the screen may display a visual signal in response to the one or more aligning sensor detecting that the user is not in the calculated optimum postural position; wherein the speaker may provide an auditory signal in response to the one or more aligning sensor detecting that the user is not in the calculated optimum postural position; and wherein the one or more initial sensor may provide a tactile signal in response to the one or more aligning sensor detecting that the user is not in the calculated optimum postural position. The indicator may also comprise one or more computer accessory; wherein the one or more computer accessory may cease to function in response to the one or more aligning sensor detecting that the user is not in the calculated optimum postural position; wherein the one or more computer accessory may function in response to the one or more aligning sensor detecting that the user has returned to the calculated optimum postural position. The one or more initial sensor and the one or more aligning sensor may comprise a means of affixing; wherein the means of affixing may comprise an adhesive, a hook and loop, a button, and a snap. The system for improving posture may comprise six initial sensors, wherein the six initial sensors may comprise: a first initial sensor, a second initial sensor, a third initial sensor, a fourth initial sensor, a fifth initial sensor, and a sixth initial sensor; wherein the first initial sensor may be configured to be located under a right sits bone of the user; wherein the second initial sensor may be configured to be located under a left sits bone of the user; wherein the third initial sensor may be configured to be located under a right foot of the user; wherein the fourth initial sensor may be configured to be located under a left foot of the user; wherein the fifth initial sensor may be configured to be located on a right shoulder of the user; and wherein the sixth initial sensor may be configured to be located on a left shoulder of the user. The software program may be configured to store data from the one or more aligning sensor; wherein the software program may be configured to provide real-time feedback on posture of the user. The software program may also be configured to analyze the information from the one or more aligning sensor and provide a suggestion of an appropriate stretch and an appropriate exercise required for the user to improve conformance with the calculated optimum postural position.

Another embodiment of the device, system, and/or method for improving posture, may comprise: six initial sensors, one or more aligning sensor, a software program, a computer, a camera, and one or more indicator; wherein the six initial sensors may be configured to monitor an initial posture of a user; wherein the six initial sensors may be configured to determine a weight, a pressure, an orientation, a heart rate, a blood pressure, a gyroscopic orientation, and a respiration of the user; wherein the six initial sensors and the one or more aligning sensor may comprise a means of affixing; wherein the means of affixing may comprise an adhesive, a hook and loop, a button, and a snap; wherein the software program may be configured to run on the computer; wherein the software program may be configured to accept information about the user; wherein the software program may be configured to accept data from the camera; wherein the software program may be configured to calculate an optimum postural position based on measurements collected by the six initial sensors, the camera, and the information about the user; wherein the one or more aligning sensor and the camera may be configured to monitor conformance of the user with the calculated optimum postural position and send information on conformance of the user with the calculated optimum postural position to the software program; wherein the one or more indicator may comprise: a screen, a speaker, one or more computer accessory, and one or more of the six initial sensors; wherein the software program may be configured to prompt the one or more indicator to provide a signal to the user; wherein the screen may display a visual signal in response to the one or more aligning sensor detecting that the user is not in the calculated optimum postural position; wherein the speaker may provide an auditory signal in response to the one or more aligning sensor detecting that the user is not in the calculated optimum postural position; wherein the one or more computer accessory may cease to function in response to the one or more aligning sensor detecting that the user is not in the calculated optimum postural position; wherein the one or more computer accessory may function in response to the one or more aligning sensor detecting that the user has returned to the calculated optimum postural position; and wherein one or more of the six initial sensors may provide a tactile signal in response to the one or more aligning sensor detecting that the user is not in the calculated optimum postural position; wherein the software program may be configured to store and analyze data from the one or more aligning sensor; and wherein the software program may be configured to provide real-time feedback on posture of the user and provide a suggestion of an appropriate stretch and an appropriate exercise that may be required for the user to improve conformance with the calculated optimum postural position. The six initial sensors may comprise: a first initial sensor, a second initial sensor, a third initial sensor, a fourth initial sensor, a fifth initial sensor, and a sixth initial sensor; wherein the first initial sensor may be configured to be located under a right sits bone of the user; wherein the second initial sensor may be configured to be located under a left sits bone of the user; wherein the third initial sensor may be configured to be located under a right foot of the user; wherein the fourth initial sensor may be configured to be located under a left foot of the user; wherein the fifth initial sensor may be configured to be located on a right shoulder of the user; and wherein the sixth initial sensor may be configured to be located on a left shoulder of the user.

These, as well as other components, steps, features, objects, benefits, and advantages, will now become clear from a review of the following detailed description of illustrative embodiments, of the accompanying drawings, and of the claims.

BRIEF DESCRIPTION OF THE ILLUSTRATIVE EMBODIMENTS

The drawings show illustrative embodiments, but do not depict all embodiments. Other embodiments may be used in addition to or instead of the illustrative embodiments. Details that may be apparent or unnecessary may be omitted for the purpose of saving space or for more effective illustrations. Some embodiments may be practiced with additional components or steps and/or without some or all components or steps provided in the illustrations. When different drawings contain the same numeral, that numeral refers to the same or similar components or steps.

FIGS. 8A-E are illustrations of several embodiments of the posture improvement system interface and shows warnings.

Figure 9:
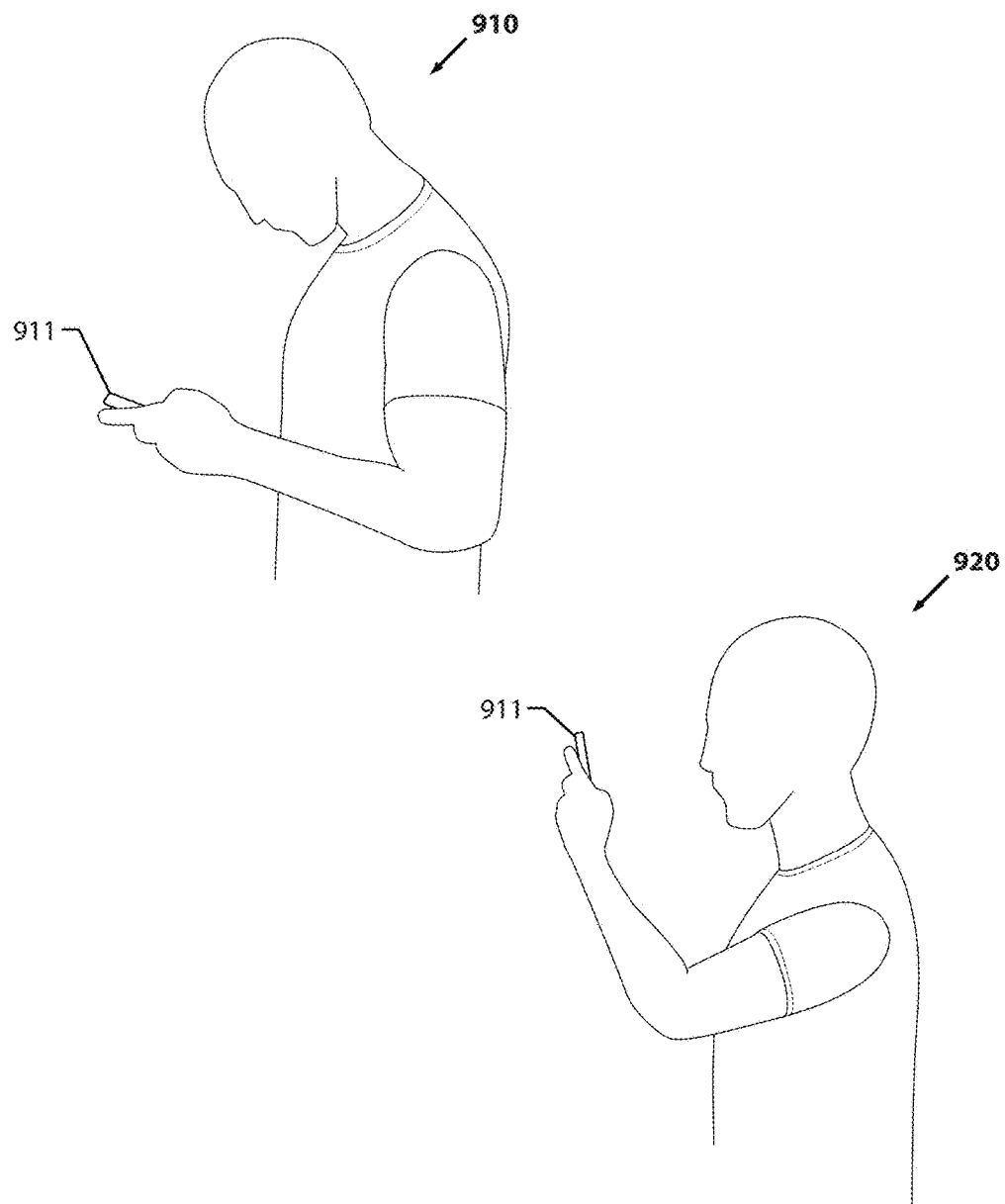

FIG. 9 is an illustration of another embodiment of the posture improvement system and shows that the system may be entirely contained on a user's mobile computing device.

Figure 10A:
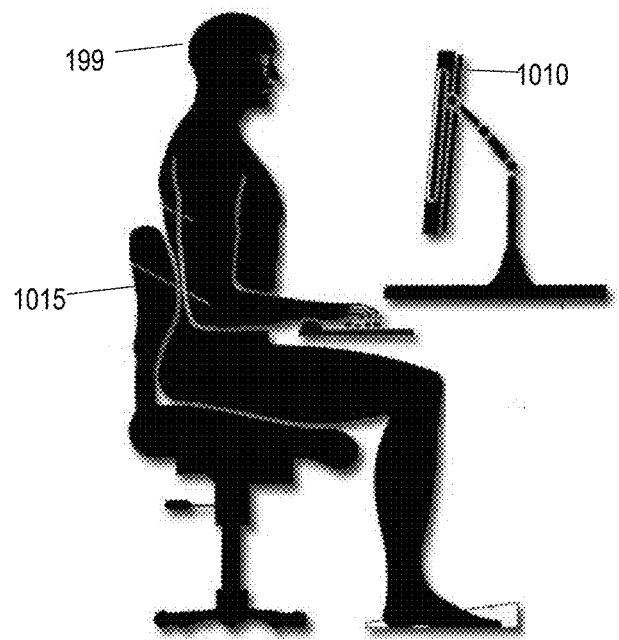

FIG. 10A is an illustration of a user sitting in his/her OPP.

Figure 10B:
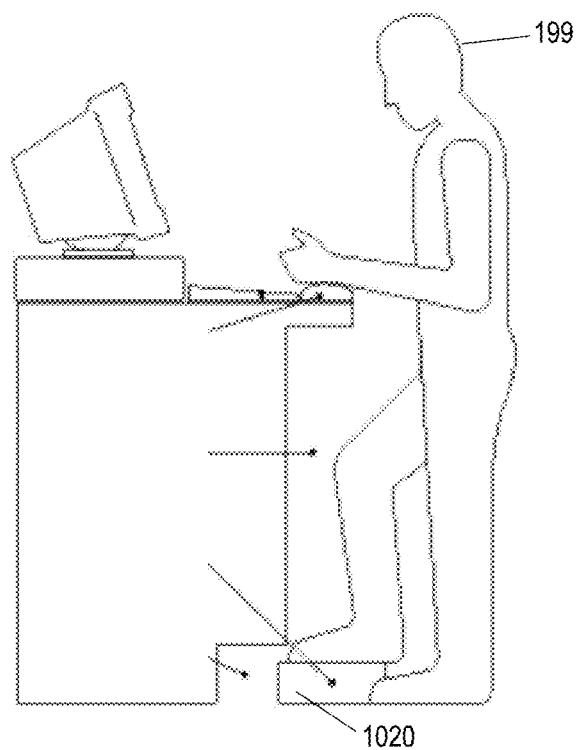

FIG. 10B is an illustration of a user standing in his/her OPP.

FIGS. 11A-C is an illustration of one embodiment of the posture improvement system interface and shows the interface providing different users with their postural behavior patterns.

Figure 12:
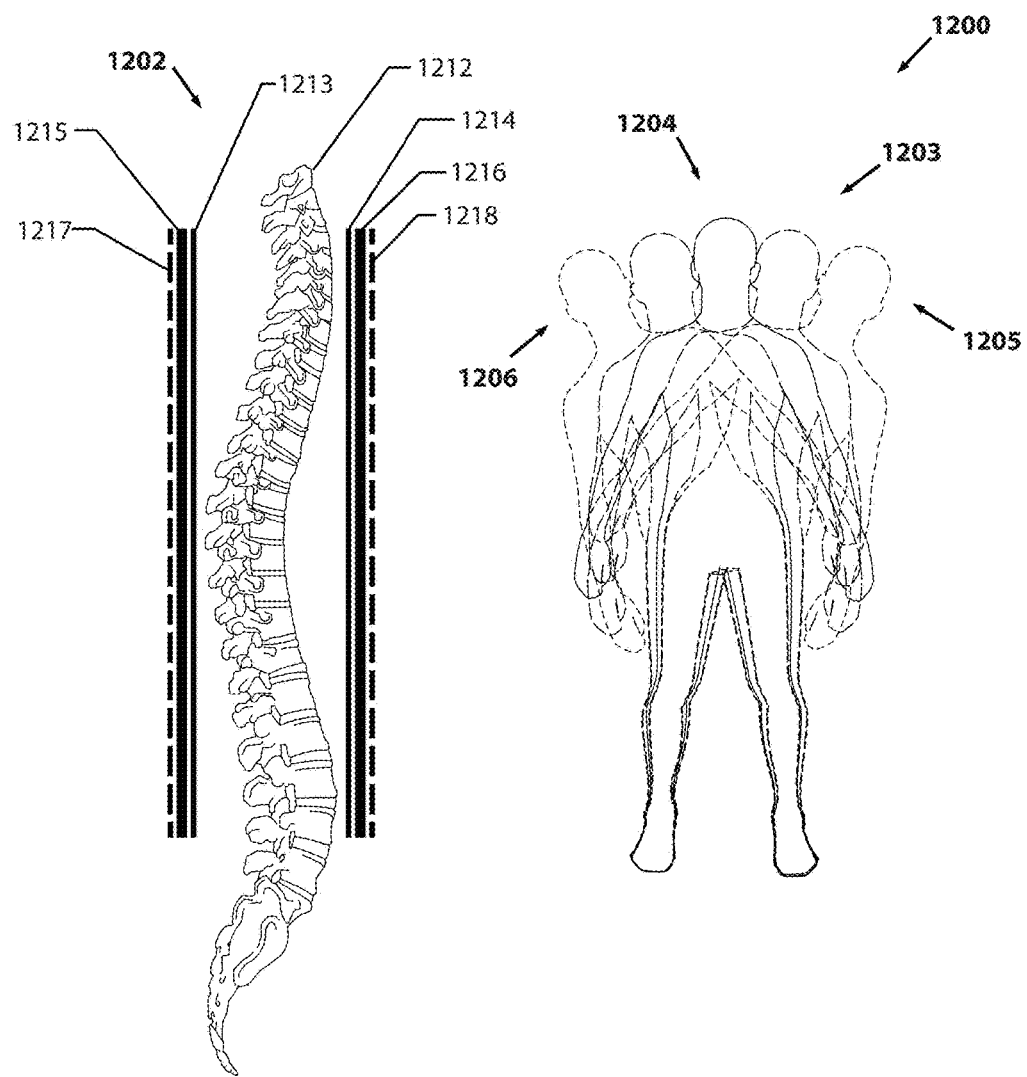

FIG. 12 is an illustration of another embodiment of the posture improvement system interface.

DETAILED DESCRIPTION OF THE ILLUSTRATIVE EMBODIMENTS

In the following detailed description, numerous specific details are set forth in order to provide a thorough understanding of various aspects of one or more embodiments. However, the one or more embodiments may be practiced without some or all of these specific details. In other instances, well-known procedures and/or components have not been described in detail so as not to unnecessarily obscure aspects of the embodiments.

While some embodiments are disclosed herein, still other embodiments will become obvious to those skilled in the art as a result of the following detailed description. These embodiments are capable of modifications of various obvious aspects, all without departing from the spirit and scope of protection. The Figures, and their detailed descriptions, are to be regarded as illustrative in nature and not restrictive. Also, the reference or non-reference to a particular embodiment shall not be interpreted to limit the scope of protection.

Definitions

In the following description, certain terminology is used to describe certain features of one or more embodiments. For example, as used herein, the terms "computer", "computing device", or "computer system" refer to any device or machine that processes data or information with an integrated circuit chip, including without limitation, personal computers, mainframe computers, workstations, testing equipment, servers, desktop computers, portable computers, laptop computers, embedded computers, wireless devices including cellular phones, personal digital assistants, tablets, tablet computers, smartphones, portable game players, and hand-held computers. Computing devices may also include mobile computing devices such as smartphones, tablets, wearables, and the like.

As used herein, the term "Internet" generally refers to any collection of networks that utilizes standard protocols, whether Ethernet, Token ring, Wi-Fi, asynchronous transfer mode (ATM), Fiber Distributed Data Interface (FDDI), code division multiple access (CDMA), global systems for mobile communications (GSM), long term evolution (LTE), or any combination thereof. The term "website" refers to any document written in a mark-up language including, but not limited to, hypertext mark-up language (HTML) or virtual reality modeling language (VRML), dynamic HTML, extended mark-up language (XML), wireless markup language (WML), or any other computer languages related thereto, as well as to any collection of such documents reachable through one specific Internet Protocol Address or at one specific World Wide Web site, or any document obtainable through any particular Uniform Resource Locator (URL).

The terms "application", "software", "software application", or "posture improvement software program" generally refer to any set of machine-readable instructions on a client machine, web interface, and/or computer system, that directs a computer's processor to perform specific steps, processes, or operations disclosed herein. The "application", "software", "software application", and "posture improvement software program" may comprise one or more modules that direct the operation of the computing device or computer system for monitoring a conformance of the user with one or more optimum postural positions. For purposes of this specification, a module may be implemented as a hardware circuit comprising custom VLSI circuits or gate arrays, off-the-shelf semiconductors such as logic chips, transistors, or other discrete components. A module may also be implemented in programmable hardware devices such as field programmable arrays, programmable array logic, programmable logic devices, and the like. Modules may also be implemented in software for execution by various types of processors. An identified module of executable code may, for instance, comprise one or more physical or logical blocks of computer instructions, which may, for instance, be organized as an object procedure, or function. Nevertheless, the executables of an identified module need not be physically located together, but may comprise disparate instructions stored in different locations, which when joined logically together, may comprise the module and achieve the stated purpose for the module.

As used herein, the term "substantially" refers to the complete or nearly complete extent or degree of an action, characteristic, property, state, structure, item, or result. For example, in one embodiment, an object that is "substantially" located within a housing would mean that the object is either completely within a housing or nearly completely within a housing. The exact allowable degree of deviation from absolute completeness may in some cases depend on the specific context. However, generally speaking the nearness of completion will be so as to have the same overall result as if absolute and total completion were obtained. The use of "substantially" is also equally applicable when used in a negative connotation to refer to the complete or near complete lack of an action, characteristic, property, state, structure, item, or result.

As used herein, the terms "approximately" and "about" generally refer to a deviance of within 5% of the indicated number or range of numbers. In one embodiment, the term "approximately" and "about", refer to a deviance of between 1-10% from the indicated number or range of numbers.

It will be appreciated that terms such as "front," "back," "top," "bottom," "side," "short," "long," "up," "down," and "below" used herein are merely for ease of description and refer to the orientation of the components as shown in the figures. It should be understood that any orientation of the components described herein is within the scope of the present disclosure.

Figure 1:
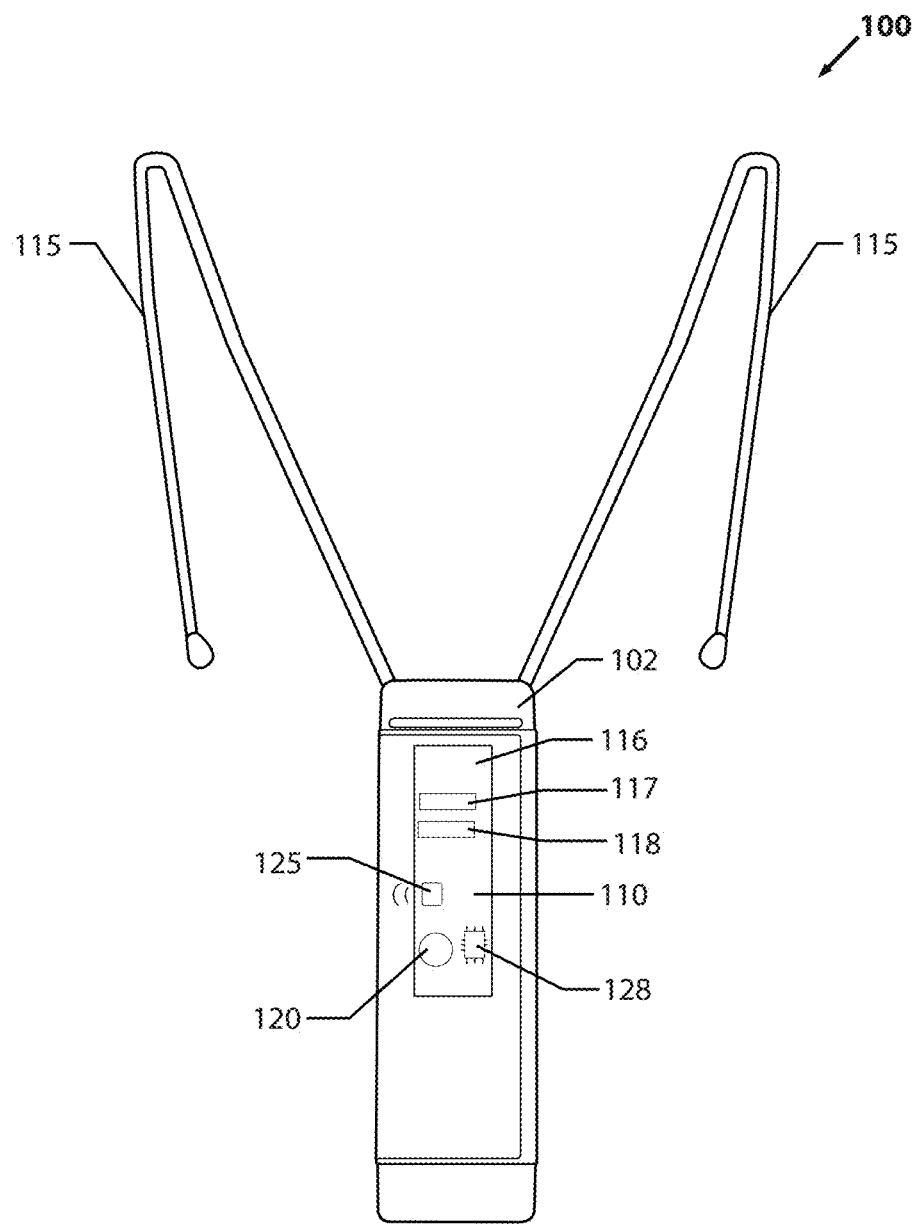
FIG. 1 is an illustration of one embodiment of the sensor device for improving posture.

FIG. 1 is an illustration of one embodiment of the sensor device for improving posture. As shown in FIG. 1, one embodiment of the sensor device 100 for improving posture may be device, wearable, or otherwise adapted to be worn or connected to the body of a user and may comprise: a minder connector 102, a minder 110, and a harness 115. The minder 110, which is also called a sensor housing or posture sensor device, may comprise: a housing 116, one or more sensors 117, 118, a power supply 120, a wireless connection device 125, and a memory unit 128. The minder connector 102 may preferably connect the minder 110 to the harness 115. As shown in FIG. 1, the harness 115 may be configured to be placed, and thereby be supported in an essentially static position on the shoulders of a user (shown in FIG. 2). For purposes of this disclosure the term harness refers to any device that allows the minder 110 to be placed between the first and the tenth thoracic vertebrae, including, but not limited to: a Y-shaped dual hook harness, a clip, a strap, a strap system, a hanging system, a hanger, a chain, an article of clothing, loop, connector, belt, band, string, tie, clamp, hitch, tether, leash, cable, hoop, and/or cord.

The sensors 117, 118 may comprise one or more axis-related accelerometers and one or more axis-related gyroscopes. The axis-related accelerometers may be primary sensors configured to measure slower movements of the user. The axis-related gyroscopes may be sensors configured to measure quick or exaggerated changes in the position of the user. Additionally, in other embodiments, the sensors 117, 118 may further comprise a pedometer, magnometer, thermometer, respiration rate meter, heart rate meter, blood pressure meter, light level meter, and/or global positioning system. In one embodiment, the accelerometers and gyroscopes may be configured to function as a pedometer, which may inform the system that the user is walking and amount of distance traveled.

The magnometer may be configured to detect the orientation of the user during his or her, the thermometer may be configured to determine both the ambient temperature and body temperature of the user, and the global positioning system may be configured to determine the physical location of the user. When multiple types of sensors are used, information gathered by the sensors may help determine multiple characteristics of the user such as his or her weight, height, pressure, orientation, heart rate, blood pressure, and respiration rate. The sensors 117, 118 may allow the system to detect any movement by the user, including forward, back, and/or side tilts, twisting, turning, bending, head position, and body alignment.

In a preferred embodiment, the minder 110 may have three tri-axial accelerometers and three tri-axial gyroscopes. Preferably, all six sensors may be used for calibration of the system, setting the optimum postural positions (OPP) of the user, and monitoring user adherence to the OPP.

Preferably, the minder 110 communicates and interfaces with an electronic data processing unit, sometimes referred to as user devices (shown in FIGS. 4 and 5), in order for the data generated by the sensors 117, 118 to be displayed to the user in an efficient and user friendly manner. In one embodiment, the minder 110 may communicate with the user devices via a low power point-to-point communication protocol such as Bluetooth®. In other embodiments, the minder may also communicate via other various protocols and technologies such as WiFi®, WiMax®, iBeacon®, near field communication (NFC), and Miracast®. In other embodiments, the minder 110 may connect in a wired manner to the user devices.

The power supply 120 may be a battery. In various embodiments, however, the power supply 120 may also comprise an additional power source, such as alternating current electrically coupled to the sensor device 100.

The memory unit 128 may be used to capture or store data when the minder 110 is not connected to a user device. In this manner, the data may be later transmitted and displayed to the user, including whether the user was maintain his/her OPP. The sensor device or user device may each house memory and process data.

Figure 2:
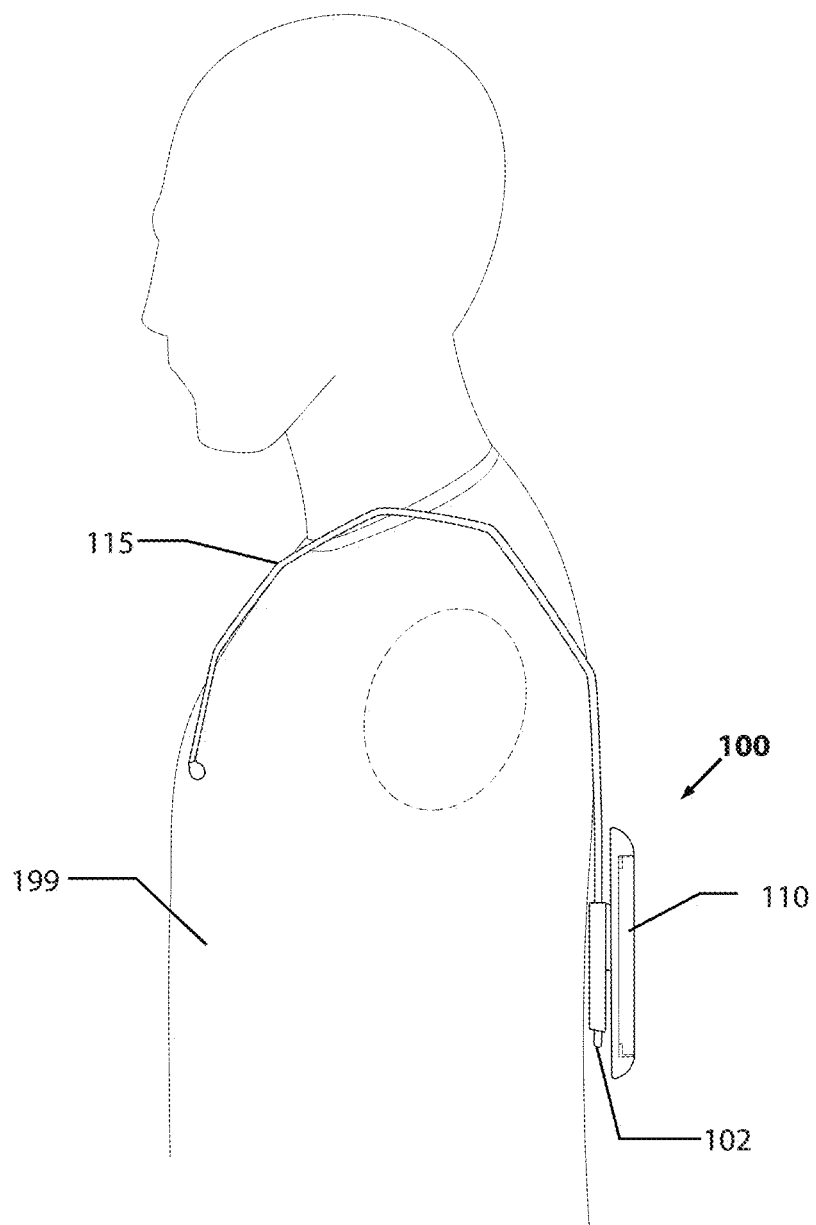
FIG. 2 is an illustration of one embodiment of the sensor device for improving posture and shows the sensor device being worn by a user.

FIG. 2 is an illustration of one embodiment of the sensor device for improving posture and shows the sensor device being worn by a user. As shown in FIG. 2, one embodiment of the sensor device 100 may be secured to the user 199 via a harness 115, such that the minder 110 is held by the minder connector 102 between the T-1 and T-10 vertebra (the first and tenth thoracic vertebra). When held in this position, the minder 110 can sense and measure almost any movement of the user 199, including head tilting, bending, twisting, turning, standing, sitting, walking, riding, biking, running, and stretching. Preferably, the harness 115 may be bendable, flexible, and/or, as preferred, poseable. In this manner, the user 199 can contour the harness 115 to his/her body structure for comfort and for maintaining the minder 110 in substantially the same place during use. In a preferred embodiment, the harness 115 may be configured to maximize user comfort. The harness may be substantially Y-shaped or may comprise a comfortable plastic coating that houses a poseable and conforming wire (or many wires laid in sequence) constructed of a shape-memory alloy. Shape-memory alloys, such as nickel titanium (NiTi), are also commonly referred to as SMA, smart metal, memory metal, memory alloy, muscle wire, or smart alloy. In this manner, the harness 115 may be heated or electrically charged, put into a specific shape and then cooled or removed from the charge, such that the harness 115 then holds this specific shape. Although FIG. 2 shows the minder 110 positioned behind the back of the user 199, as is preferred, the minder 115 may be held in other different locations, such as the front or sides of the user 199.

Figure 3:
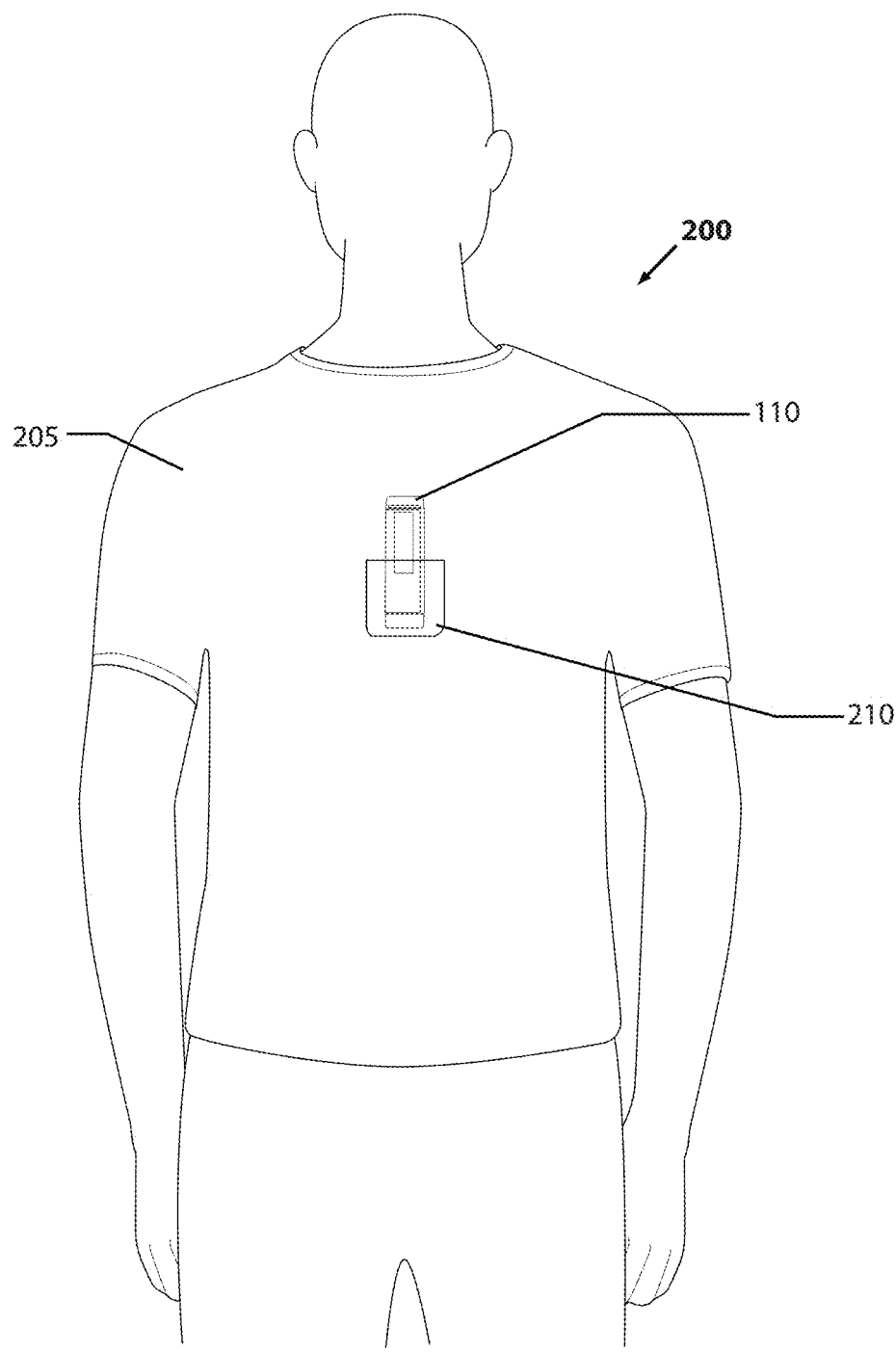
FIG. 3 is an illustration of one embodiment of the sensor device for improving posture and shows the sensor device integrated into a user's clothing.

FIG. 3 is an illustration of one embodiment of the sensor device for improving posture and shows the sensor device integrated into a user's clothing. As shown in FIG. 3, another embodiment of the sensor device 200 may be a shirt 205 that is worn by user 199. The shirt 205 may have the minder 110 integrated or sewn into the shirt, or the minder 110 may be removable and held within a pocket 210 of the shirt. The minder 110 preferably comprises a warning and sensor feature that allows the minder 110 to notify the user when the minder 110 is attached to an article of clothing that is doffed. This may help prevent the user 199 from accidentally leaving the minder 110 on the clothing before being put in the washing machine when the user washes his or her clothes. Although FIG. 3 shows the minder 110 positioned behind the back of the user 199, as is preferred, the minder 110 may be held in different locations, such as the front or sides of the user 199.

In other embodiments, the minder 110 may have an outer shell that is substantially, or partially, malleable and poseable. This may allow the user 199 to place the minder 110 in the correct position on his/her body, and then press against the minder 110, such that the outer shell of the minder 110 conforms to the user 199. This may make it much more comfortable for the user 199 to wear the posture device 100, 200 for long periods of time, and it may assist the minder 110 in maintain the correct position relative to the user 199. The malleable and poseable material may be a putty type material. In one embodiment the user 199 may form the malleable and poseable outer shell by lying on his/her back or pressing his/her back up against a wall.

Figure 4:
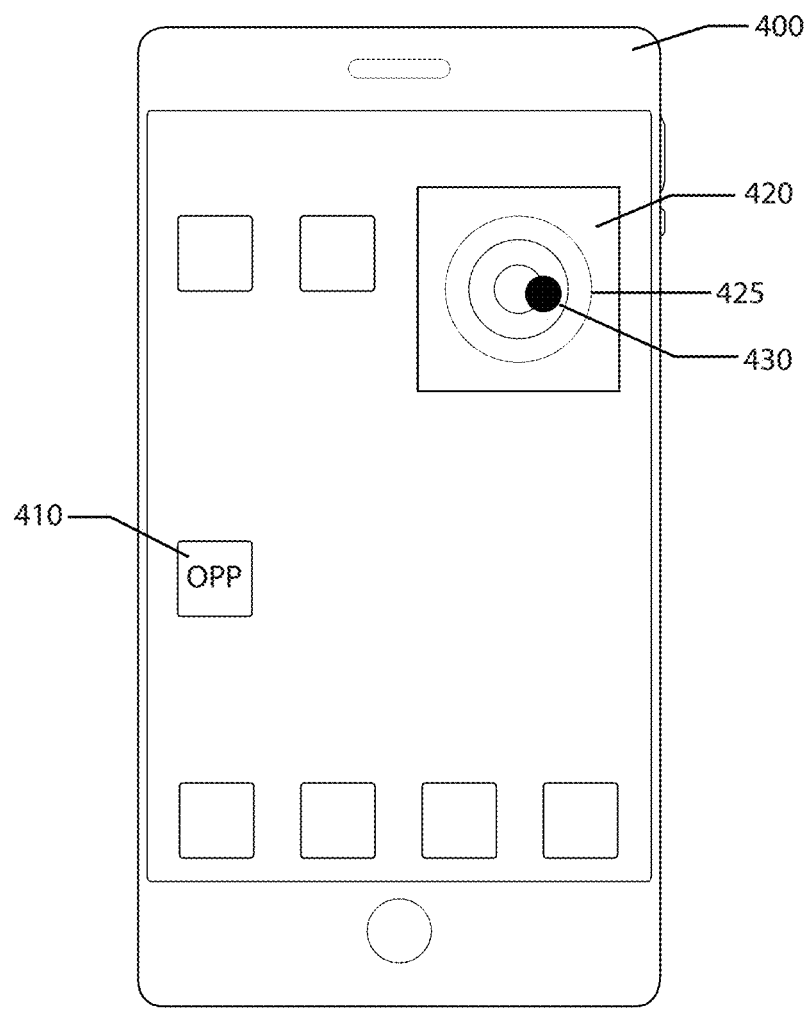
FIG. 4 is an illustration of one embodiment of the posture improvement system interface and shows the user device as a smart phone.

FIG. 4 is an illustration of one embodiment of the posture improvement system interface and shows the user device as a smart phone.

Figure 5:
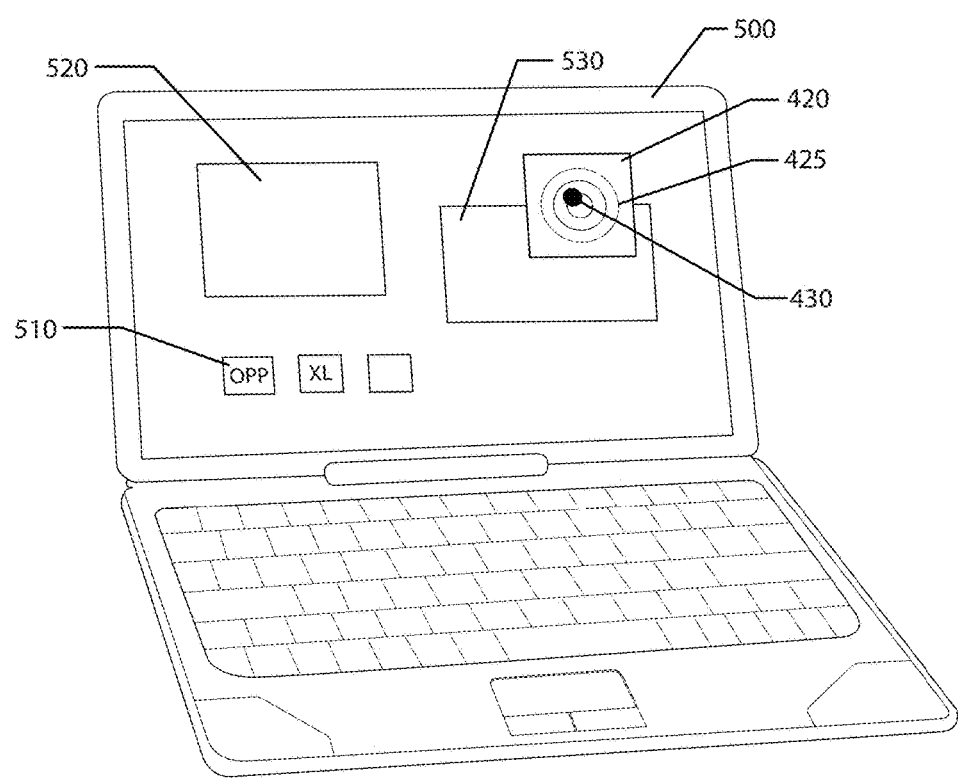
FIG. 5 is an illustration of one embodiment of the posture improvement system interface and shows the user device as a laptop computer.

FIG. 5 is an illustration of one embodiment of the posture improvement system interface and shows the user device as a laptop computer. As shown in FIGS. 4 and 5, one embodiment of the posture improvement system interface 420 may be displayed on the display screen of a user device. In this manner the user may receive real time warnings and updates from the posture device 100, 200. Although FIGS. 4 and 5 show the user devices 400, 500 as a smart phone and laptop computer, the user device may be other computing devices, such as a smart watch, a keyboard, a mouse, eyewear, a tablet, a chair, a monitor, a smart television, or some other device that is used or worn by a user.

FIGS. 4 and 5 also show that the posture improvement system may comprise a user device 400, 500, which operates and displays a posture improvement system interface 420. The system interface 420 may comprise an OPP layout 425 (such as a bullseye, target, concentric circles, a pictograph (which may be relevant such as a spine that a user tries to keep in an optimum graphical shape) and a posture target ball 430, which is shown as a ball, but may be any shape. For purposes of this disclosure the terms bullseye and target may mean the same thing. In various embodiments, the posture improvement system may be a software application 410, 510 running on the user device 400, 500 that interfaces wirelessly with the minder 110 in order to determine whether the user is maintaining his/her OPP. FIGS. 4 and 5 also show that the system interface 420 may be displayed in the background or foreground of the display screen of the user device 400, 500. When in the foreground, the system interface 420 may overlap another program 530. Although system interface 420 is shown as a concentric circle target 425 and posture target ball 430, it should be understood that other shapes or graphics could be used, so long as the user is provided with information regarding the maintenance of his/her OPP. The system interface 420 may provide a user friendly depiction of one's posture by displaying the posture of the user through a simple, visual depiction.

Figure 6:
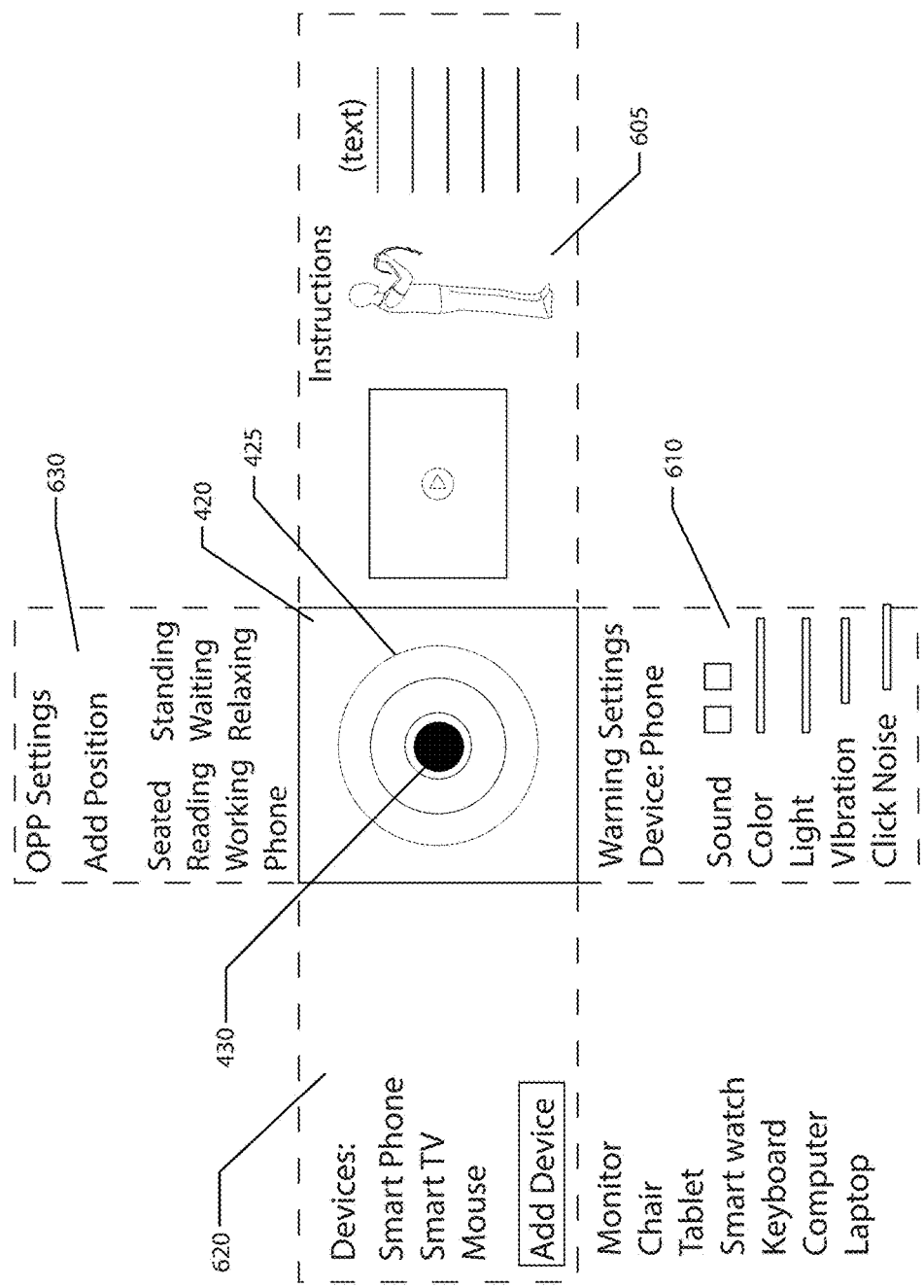
FIG. 6 is an illustration of one embodiment of the posture improvement system interface and shows pop up interface windows.

FIG. 6 is an illustration of one embodiment of the posture improvement system interface and shows pop up interface windows. As shown in FIG. 6, one embodiment of the system interface 420 may comprise an OPP layout 425, a posture target ball 430, an instructions screen 605, a warning settings screen 610, a devices screen 620, and an OPP settings screen 630. The additional screens 605, 610, 620, and 630 may be displayed when needed and hidden when not needed to provide an uncluttered look to the system interface 420. The system interface 420 may appear similar to a level with a digital bubble.

In one embodiment, the instructions screen 605 may be positioned to the right of the system interface 420 and may provide instructions for calibrating and using the posture system. The instructions may be provided in any form, including text, videos, graphics, flow charts, and/or pictures. The instructions screen 605 or another screen that is part of the software program may allow the user to set up and/or calibrate the posture system. Preferably, the set up and calibration may be accomplished through a decision tree or wizard that takes the user step-by-step through the process. In one embodiment, the system may prompt the user to input basic information such as his or her height and weight. The user may also input information regarding any pain the user may be experiencing. Upon receiving the information from the user, the software program may prompt the user to place the minder 110 in the proper position. In an additional embodiment, the software program may provide the user with textual, pictorial, or video instructions 605 in order to further guide the user to the proper position for the minder 110.

The warning settings screen 610 may allow the user to set and change the warnings used by the system interface 420 for notifying the user when he/she is not in OPP. For example, in one embodiment, the user may first select the appropriate device for setting the warnings. The presentation of devices may be related to the devices screen 620. Once a device is selected, such as a phone, as shown in FIG. 6, the user may then select how the phone will warn the user of misalignment or when the user is not in his/her OPP. In various embodiments, the user may choose to be notified or warned via sound notification, change in color, flash of light or change in brightness, vibration, current or shock, other type of sensory warning, or a change in the functionality of the device. Preferably, the user sets the warnings for each device loaded in the devices screen. All warnings may be adjustable. For example, the volume of the sound warning may also be adjustable, and the brightness of the flash of light may also be adjustable. Additional colors may be selected. The strength of the vibration may be adjustable.

The devices screen 620 may allow a user to select those user devices that will communicate with the sensor device 100, 200. The user devices may include, but are not limited to: a smart phone 400, laptop computer 500, a smart watch, a keyboard, a mouse, a tablet, a chair, a monitor, eyewear, a smart television, or some other device that is used or worn by a user. In some embodiments, there is no real time user device, and the warnings are provided directly by the sensor device 100, 200. In this manner, the sensor device 100, 200 may directly warn the user via sound, light, touch (poke), vibration, and/or click. The sensor device 100, 200 may include an integrated additional device that provides such a warning, or one of the existing portions of the sensor device 100, 200 may provide the warning.

The OPP settings screen 630 may allow the user to select one or more positions to associate with an OPP. The positions are various seated, standing, and active positions, including, but are not limited to: watching media (including, but not limited to, phone, tablet, television, and virtual reality imaging); sport/activity (including, but not limited to, walking, running, cycling, golf, baseball, basketball, yoga, snowboarding, skiing, and football); driving; working, including, but not limited to, telephone, computer, and stand up desk); hospital bed/bed ridden; travel (airplane travel); interactive games (computer and board games); presentations; personal confidence; repetitive occupational motion; specific occupational needs. Once the OPP settings are inputted into the system, the user may then calibrate each of the OPP by donning the sensor device 100, 200 and assuming the approximate correct position.

Once the posture improvement system is calibrated and set up, the user may use the system to ensure that the OPP is maintained during use. This is done by activating and donning the sensor device 100, 200. The user must also select a user device and open the system interface 420 on that device. The system interface 420 may then inform the user whether his/her OPP is being maintained (see FIG. 8).

In one embodiment, the system interface 420 may alert the user to take periodic activity breaks, such as standing and/or stretching. The system interface 420 may also suggest a particular activity for the user to engage in during the activity break based on information regarding user pain and user conformance to his/her OPP.

Preferably, the user may switch from one OPP to another. This switch may be manual inputted by the user, thereby informing the system of the change. The switch may also be automatic, such that the minder 110 determines that the user has switched positions and intuitively changes to the more correct and appropriate OPP. This automatic switch preferably allows the user to confirm or reject the automatic switch. Regarding the automatic switch, in one embodiment, the system includes: a sensor device; and a posture improvement software program installed on multiple user devices, which possesses a notification system of OPP and an OPP display. This embodiment highlights the need for a smart and seamless network recognition system of the multiple user devices, such that the user is notified only on the appropriate user device. The description of "appropriate user device" in this embodiment is described by: proximity to other user devices, level and or the activity of the user, and user devices in use. In one example, where the seamless networking recognition system utilizes proximity as the primary factor for user device selection, a user working at a computer will have the posture improvement software displayed on the computer screen. Once the user discontinues work and leaves the proximity of the computer, the posture improvement software is no longer required to be running on the computer. The sensor device seamlessly transitions the posture improvement software system to display on the next appropriate user device. This user device may be a smart phone, a tablet computer, a smart watch, other wearable devices, or other suitable device for OPP notification display or activity. Furthermore, the sensor device or the user device may relay information regarding active use of specific user devices as a mechanism for seamless network sensing (i.e. proximity to a computer workstation and/or the user is engaged in active use of a smart phone for an extended period, therefore, the posture improvement software displays on the smart phone). In another example, where a user chooses to engage in exercise by running, the activity level and pattern of movement detected by the sensor device will select a smart watch as the most appropriate user device, as opposed to a smart phone. In addition to these examples, a hybrid model that utilizes both proximity and activity may also be used to determine the appropriate device in which to activate the interface. In various embodiments, seamless switching between devices may be performed either automatically by the sensor, or manually selected by the user. In addition, seamless switching determination may be performed by the sensor device, or the user devices.

Figure 7:
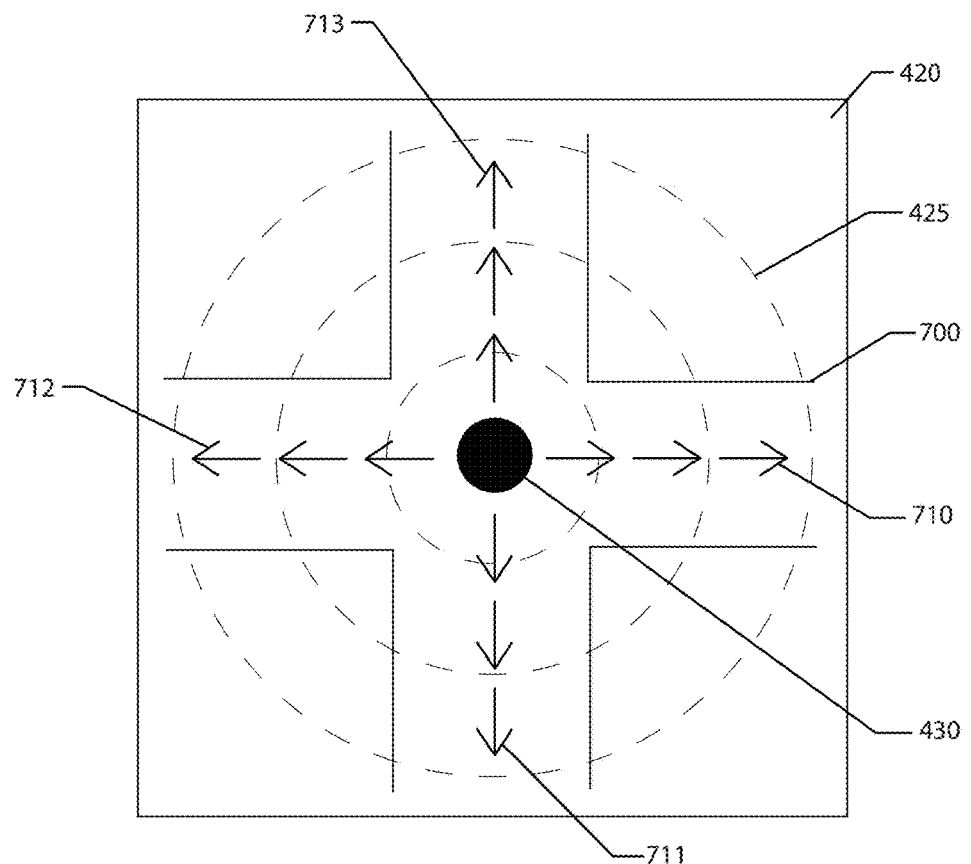
FIG. 7 is an illustration of one embodiment of the posture improvement system interface and shows an activity display.
Figure 8:
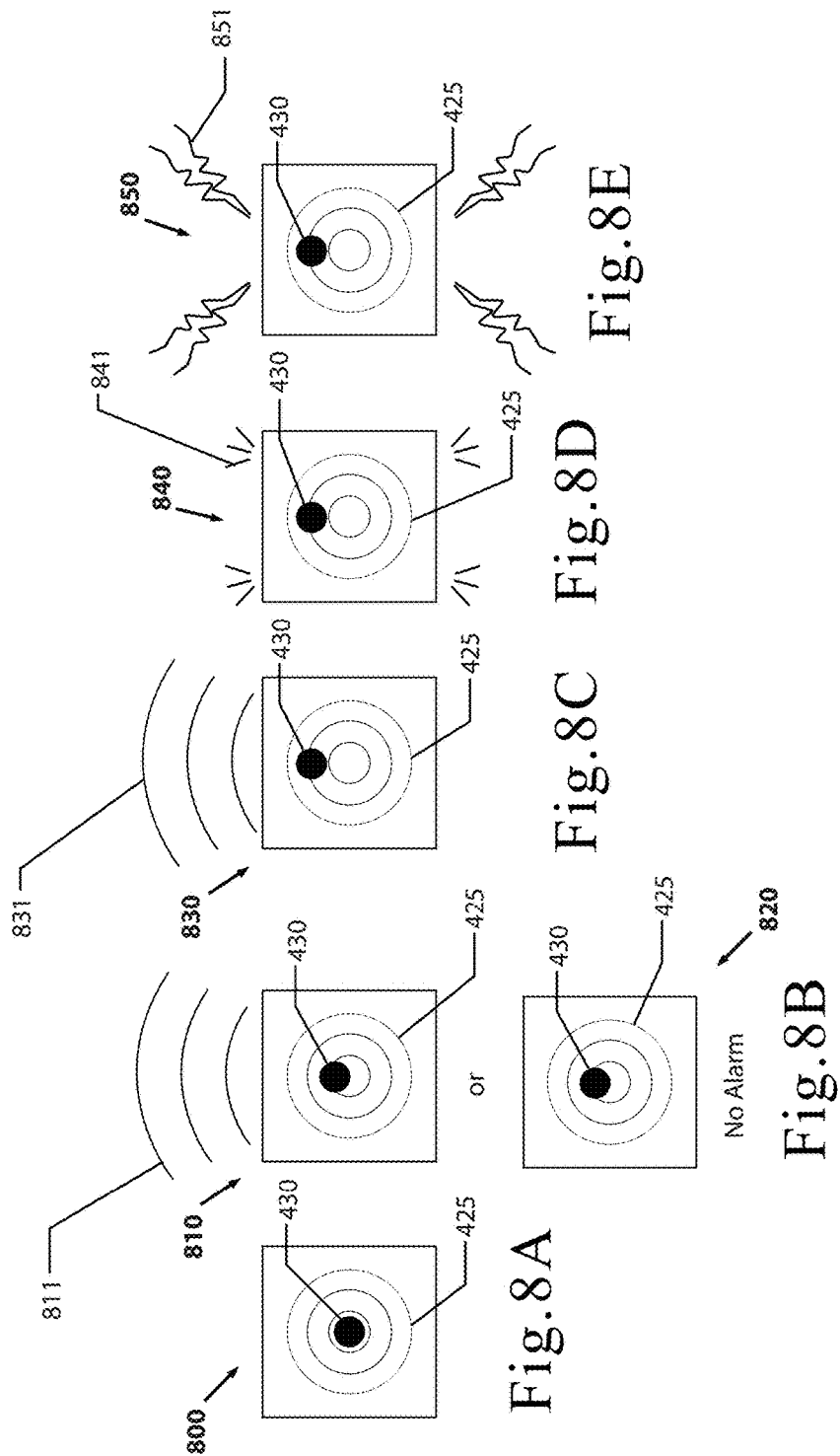

FIG. 7 is an illustration of one embodiment of the posture improvement system interface and shows an activity display. As shown in FIG. 7, one embodiment of the system may require that the user take a periodic activity break. In one embodiment, the user is required to stretch in various directions. The target 425 of system interface 420 may be overlaid with a crosshair 700. The system may then require that the user move the posture target ball 430 within the crosshair 700 in the direction of the arrows 710, 711, 712, 713. This may be performed by having the user stretch to the right, back, left, and forward, which concurrently moves the posture target ball 430 in the correct direction within the crosshair 700. This gamification of taking a break may prompt the user to actually comply with the request of taking an activity break. The periodic activity reminders may be set for any period, including, but not limited to, once every ten minutes, once every twenty minutes, once every thirty minutes, once an hour, and the like. In other embodiments, the user may be required to follow the ball to get to the target exercise or stretch position.

FIGS. 8A-E are illustrations of several embodiments of the posture improvement system interface and shows warnings. As shown in FIGS. 8a-e, one embodiment of the system displays the system interface 420 to the user. When the user is physically maintaining his/her OPP 800, the posture target ball 430 may be at the center of the target 425. When OPP is not maintained as shown in the interfaces 810, 830, 840, 850, in FIGS. 8B-E, the posture target ball 430 may move out of the center of the target 425, and alarm, such as a sound 811, 831, flash of light or color change 841, vibration 851, or a change in the functionality of a user device may activate. Preferably, the sensitivity of the alarm is adjustable. The sensitivity, for example, may be very high, such that when as little as 1% of the posture target ball 430 moves out of the center of the target 425, the alarm may activate. The sensitivity may also be set very low, such that the entire posture target ball 430 must leave the center of the target 425 in order to activate the alarm. Interface 810 shows a high sensitivity setting, in which an alarm has sounded. Interface 820, on the other hand, shows a low sensitivity setting, in which the posture target ball has moved the same as posture improvement system interface 810 without activating the alarm.

Allowing the user to adjust the sensitivity, which, in one embodiment, may simply be pulled up and manipulated from interface 420, preferably helps eliminate beginner frustration from having multiple alarms activate. One of the benefits of the posture improvement system is preferably creating a fun and challenging game for the user to keep his/her posture within the OPP. This makes it much more likely that the user will actually use the device to improve his/her posture.

The configuration of the system to issue alarms may help train the user to use OPP through behavioral modification and negative feedback. By alarming, prodding, and repeatedly reminding the user of improper posture, the system is ensuring that the user is aware of when he/she is not in OPP. Additionally, because the alarm does not cease until the user is in his/her OPP, the user may learn to practice his/her OPP after repeated exposure to the alarm.

In one embodiment, the posture improvement system has a multi-stage alarm or series of alarms, wherein the first alarm may be a change in interface screen color. The user may be able to view the color change via peripheral vision, and make minor corrections to maintain the posture target ball 430 in the very center of target 425. This "game" of keeping the ball 430 in the dead center of target 425 is an important aspect of making the possibly very strenuous task of maintaining perfect OPP, a fun game, which significantly increases the chance that the user continue to use the posture improvement system. In another embodiment, the posture improvement system has a second alarm that activates if the first alarm is repeatedly ignored or if the posture target ball 430 misaligns past a certain point, such as if the posture target ball 430 completely leaves the smallest concentric circle of target 425, as shown in FIG. 8E. This second alarm may preferably be a more obtrusive alarm, such as a vibration or sound, which the user has a harder time ignoring.

FIG. 8A shows that the posture target ball 430 may preferably be smaller than the smallest concentric ring of target 425, such that the user may keep the entire target ball 430 within the smallest concentric ring.

FIG. 9 is an illustration of another embodiment of the posture improvement system and shows that the system may be entirely contained on a user's mobile computing device. As shown in FIG. 9, the posture improvement software may utilize the existing accelerometers and gyroscopes of a mobile computing device 911 in order to improve a user's posture. When a user lowers his/her head as shown in 910 when using a mobile computing device 911, the posture improvement system may temporarily disable the mobile computing device 911 until the user brings the mobile computing device 911 up as shown in 920. This alternative embodiment does not generally require the sensor device 100, 200, and it is directed primarily to having the user raise his/her head while using a mobile computing device 911.

In another embodiment, the software program may prompt the user to navigate to a website. This may allow a professional to see the user via a camera. This professional may then be able to assist the user in establishing the OPP. Additionally, in another embodiment, the posture improvement system may be integrated into the larger health improvement goals of a user, including a diet or exercise program.

In one embodiment, the posture improvement software, in addition to providing real-time feedback via the interface 420, may store the alignment/misalignment data, such that the user can view the data and/or create graphs or reports, which may assist a user in understanding how to improve his/her posture. In this manner, the user can track his/her posture progress and work on any issues that repeatedly occur. The user may also be able to compare his/her progress with that of other users, which may further encourage the users to improve their posture based on the competition that may arise.

FIG. 10A is an illustration of a user sitting in his/her OPP. When the user 199 is sitting in front of a screen 1010, as shown in FIG. 10A, OPP is determined to be the position at which the user 199 is seated on a chair 1015 with both knees at a 90° degree angle and both feet placed flat on the ground. The back of the user should also lie substantially flat against the vertical back of the chair 1015. Additionally, the screen 1010 may be positioned approximately eye level of the user.

FIG. 10B is an illustration of a user standing in his/her OPP. As shown in FIG. 10B, the OPP of user 199 while standing may occur when the user 199 is standing with his/her back substantially straight and with his/her feet substantially flat on a surface. Additionally, in other embodiments, a footrest 1020 may be used. The footrest 1020 may be placed beneath a foot of the user 199 while the other foot of the user remains behind the footrest 1020. In the event a footrest 1020 is used, OPP may occur when the user 199 alternates which foot he/she places on the footrest 1020.

FIGS. 11A-C is an illustration of one embodiment of the posture improvement system interface and shows the interface providing different users with their postural behavior patterns. FIGS. 11A-C show that the posture improvement system may include a conditioning program. After gathering data on a user's behavior, such as a user's ability, or inability, to keep the posture target ball within the target, the conditioning program analyzes the data and presents it to the user, such that the user can recognize their own postural behavior patterns. The conditioning program uses temporal tracking of the target ball which allows the conditioning program to select a specific conditioning activity to correct improper posture. FIG. 11A shows that User 1 1101 has very good postural behavior and the pattern 1111. Accordingly, the conditioning program recommends a basic stretch interval program. FIG. 11B shows that User 2 1103 has good postural behavior and the pattern 1113, but there is room for improvement. User 2 1103 frequently leans forward and to the right. The conditioning program selects or creates an interval program, which is also referred to as a conditioning regimen or activity interval program, which matches with User 2's deficiencies. FIG. 11C shows that User 3 1105 has good postural behavior and the pattern 1115, but there is room for improvement. User 3 1105 frequently leans back and to the left. The conditioning program determines whether the user is just leaning against the chair or has a more severe bad posture behavior. If just leaning back, then a basic stretch interval program is recommended by the conditioning program. If bad posture, the conditioning program selects a more appropriate conditioning regimen is created or selected that matches with User 3's deficiencies.

Another embodiment of the posture improvement system may comprise a program for gradually improving posture and may comprise: a smart phone or other user device; a posture improvement software program operating on the smartphone or other user device; and information gathered by the user regarding physical body type and size, physical capabilities, and goals of the user. The information gathered from the user may be utilized by the posture improvement software program to form a gradual exercise, stretch, and conditioning program such that proper posture achieved in a safe manner. The gradual conditioning program may be separated into three consecutive phases: stretch and activity phase; time spent in perfect posture (OPP) phase; and a phase of good, but relaxed, posture. The gradual conditioning program may determine, preferably through an algorithm the ratio of time to be spent in each phase, such that the user may gradually build muscle capacity to perform the OPP phase for longer periods of time. Example 1: if the user is really strong then the program may comprise a 5 minute stretch, 30 minutes OPP, and 25 minutes relaxed posture (cycle time 1 hour). Over time, the program may change to a 5 minute stretch, 50 minutes OPP, and a 5 minute relaxed posture, and so on. Example 2: if the beginning user is relatively weak with limited mobility, the program may start with a 10 minute stretch, 10 minutes of OPP, and 40 minutes of relaxed posture. Over time, the program may increase difficulty to 10 minutes of stretch, 20 minutes of OPP, and 30 minutes relaxed posture, and so on. This embodiment may also include an intensive conditioning program at the initiation of an OPP setting—i.e. at a work station. This feature may require a higher ratio of perfect posture time phase, and less time spent in stretch and relaxed posture. Subsequently, the gradual conditioning program will be resumed for the remainder of time spent at the workstation.

FIG. 12 is an illustration of another embodiment of the posture improvement system interface. FIG. 12 shows that the posture improvement system interface 1200 may comprise two interface graphics 1202 and 1203 presented side by side. In one embodiment, graphic 1202 may be a side view of a spine 1212. As the user tilts or hunches in a forward and backward manner, the minder relays these movements to the interface 1200 and the movements are shown in graphic 1202. When the user maintains OPP, the spine 1212 is within first parameter 1213, 1214. When the user fails to maintain OPP, the spine 1212 graphic is shown crossing first parameter 1213, 1214. When this happens a first alarm may activate. The first alarm may preferably be the first parameters 1213 and/or 1214 lighting up or turning a specific color. If the user moves significantly out of alignment in a forward or backward manner, the spine 1212 graphic may be shown to cross second parameters 1215, 1216 and/or third parameters 1217, 1218. When this happens a second, third, fourth, or more alarms may activate. These additional alarms may be color changes or lighting up of parameters 1215, 1216, 1217, 1218, sounds, vibrations, or even disablement of user device(s).

FIG. 12 also shows that interface graphic 1203 may be a forward or rear view of an avatar 1204 of the user. As the user leans to the left or the right, the minder relays these movements to the interface 1200 and the movements are shown in graphic 1204. When the user maintains OPP, the avatar is shown in an optimal straight position. FIG. 12 shows that the avatar mirrors the user's left and right 1205, 1206 leaning, as the user leans in real life. When the user leans too much to the left or the rights one or more alarms may activate to notify the user that he or she is not maintaining OPP.

In one embodiment of the posture improvement system, the conditioning program automatically (preferably via an algorithm) determines the relaxed posture position from the OPP.

Unless otherwise stated, all measurements, values, ratings, positions, magnitudes, sizes, locations, and other specifications that are set forth in this specification, including in the claims that follow, are approximate, not exact. They are intended to have a reasonable range that is consistent with the functions to which they relate and with what is customary in the art to which they pertain.

The foregoing description of the preferred embodiment has been presented for the purposes of illustration and description. While multiple embodiments are disclosed, still other embodiments will become apparent to those skilled in the art from the above detailed description, which shows and describes the illustrative embodiments. These embodiments are capable of modifications in various obvious aspects, all without departing from the spirit and scope of protection. Accordingly, the detailed description is to be regarded as illustrative in nature and not restrictive. Also, although not explicitly recited, one or more embodiments may be practiced in combination or conjunction with one another. Furthermore, the reference or non-reference to a particular embodiment shall not be interpreted to limit the scope of protection. It is intended that the scope not be limited by this detailed description, but by the claims and the equivalents to the claims that are appended hereto.

Except as stated immediately above, nothing that has been stated or illustrated is intended or should be interpreted to cause a dedication of any component, step, feature, object, benefit, advantage, or equivalent, to the public, regardless of whether it is or is not recited in the claims.

What is claimed is:

1. A system for improving posture, comprising:
   a sensor device;
   a posture improvement software program, comprising a posture improvement system interface; and
   one or more user devices;
   wherein said sensor device is configured to be physically associated with a user;
   wherein said sensor device communicates with said posture improvement software program;
   wherein said sensor device comprises: one or more sensors;
   wherein said one or more sensors, when said sensor device is physically associated with said user, monitor a physical position of said user and one or more movements of said user;
   wherein said posture improvement software program is configured to operate on said one or more user devices;
   wherein said posture improvement system interface is displayed to said user on said one or more user devices;
   wherein said posture improvement software program is configured to collect information about said user;
   wherein said system for improving posture calculates one or more optimum postural positions for said user, based on data communicated by said sensor device and said collected information about said user;
   wherein said system for improving posture monitors a conformance of said user with at least one of said one or more optimum postural positions;
   wherein said system for improving posture displays said conformance on said posture improvement system interface;
   wherein said posture improvement system detects and notifies said user of one or more non-conformances, such that a user is reminded to maintain said at least one of said one or more optimum postural positions; and
   wherein said displaying of said conformance of said user with at least one of said one or more optimum postural positions is illustrated via a target and a posture target ball.

2. The system for improving posture of claim 1, wherein said posture target ball is substantially within a center of said target when said user is in said conformance with said at least one of said one or more optimum postural positions.

3. The system for improving posture of claim 2, wherein when said user fails to maintain said at least one of said one or more optimum postural positions, said posture target ball is not substantially within said center of said target and said posture improvement system interface notifies said user of said one or more non-conformances.

4. The system for improving posture of claim 3, wherein when said user fails to maintain said at least one of said one or more optimum postural positions, said user device is substantially disabled until said user corrects said non-conformance.

5. The system for improving posture of claim 1, wherein said posture improvement software program further comprises an activity notification.

6. The system for improving posture of claim 5, wherein said activity notification requires said user to perform a body movement of said user such that said target posture ball moves along a suggested path on said target.

7. A system for improving posture, comprising:
   a sensor device;
   a posture improvement software program, comprising a posture improvement system interface; and
   one or more user devices;
   wherein said sensor device is configured to be physically associated with a user;
   wherein said sensor device communicates with said posture improvement software program;
   wherein said sensor device comprises: one or more sensors;
   wherein said one or more sensors, when said sensor device is physically associated with said user, monitor a physical position of said user and one or more movements of said user;
   wherein said posture improvement software program is configured to operate on said one or more user devices;
   wherein said posture improvement system interface is displayed to said user on said one or more user devices;
   wherein said posture improvement software program is configured to collect information about said user;
   wherein said system for improving posture calculates one or more optimum postural positions for said user, based on data communicated by said sensor device and said collected information about said user;
   wherein said system for improving posture monitors a conformance of said user with at least one of said one or more optimum postural positions;
   wherein said system for improving posture displays said conformance on said posture improvement system interface;
   wherein said posture improvement system detects and notifies said user of one or more non-conformances, such that a user is reminded to maintain said at least one of said one or more optimum postural positions;
   wherein said posture improvement software system comprises a conditioning program;
   wherein said conditioning program recommends an interval program based on a postural behavior of said user; and wherein said conditioning program provides insight to said user regarding said postural behavior of said user.

8. A system for improving posture, comprising:

a sensor device;

a posture improvement software program, comprising a posture improvement system interface; and one or more user devices;

wherein said sensor device is configured to be physically associated with a user;

wherein said sensor device communicates with said posture improvement software program;

wherein said sensor device comprises: one or more sensors;

wherein said one or more sensors, when said sensor device is physically associated with said user, monitor a physical position of said user and one or more movements of said user;

wherein said posture improvement software program is configured to operate on said one or more user devices;

wherein said posture improvement system interface is displayed to said user on said one or more user devices;

wherein said posture improvement software program is configured to collect information about said user;

wherein said system for improving posture calculates one or more optimum postural positions for said user, based on data communicated by said sensor device and said collected information about said user;

wherein said system for improving posture monitors a conformance of said user with at least one of said one or more optimum postural positions;

wherein said system for improving posture displays said conformance on said posture improvement system interface;

wherein said posture improvement system detects and notifies said user of one or more non-conformances, such that a user is reminded to maintain said at least one of said one or more optimum postural positions; and wherein a sensitivity of said notifying of said one or more non-conformances is adjustable.

* * * * *